United States Patent [19]
Liakumovich et al.

[11] 3,951,754
[45] Apr. 20, 1976

[54] METHOD OF INHIBITING THE THERMOPOLYMERIZATION OF ISOPRENE AND BUTADIENE

[76] Inventors: Alexandr Grigorievich Liakumovich, prospekt Lenina, 23, kv. 4; Boris Izrailevich Pantukh, prospekt Oktyabrya, 6, kv. 97; Aida Pavlovna Zakharova, ulitsa Druzhby, 19, kv. 11, all of Sterlitamak; Vitaly Ivanovich Butin, Molodezhny Butvar, 33, kv. 31, Tolyatti; Vladimir Alexeevich Tulupov, ulitsa Krasny Mayak, 4, korpus 2, kv. 33, Moscow; Zoya Stephanovna Baiburina, ulitsa Volochaevskaya, 16-a, Kv. 19, Sterlitamak, all of U.S.S.R.

[22] Filed: Feb. 19, 1974

[21] Appl. No.: 433,777

Related U.S. Application Data

[63] Continuation of Ser. No. 164,127, July 19, 1971, abandoned.

[52] U.S. Cl............................... 203/9; 203/32; 203/33; 203/38; 203/59; 203/62; 203/63; 260/666.5; 260/681.5 R
[51] Int. Cl.$^2$...................... B01D 3/00; C07C 7/18
[58] Field of Search.................. 203/9, 8, 6, 32, 33, 203/38, 59, 62, 63; 260/681.5 R, 666.5

[56] References Cited
UNITED STATES PATENTS

| | | | |
|---|---|---|---|
| 2,491,732 | 12/1949 | Hawkinson | 203/86 |
| 2,888,386 | 5/1959 | Brower | 203/9 |
| 2,900,421 | 8/1959 | Kharach | 203/9 |
| 2,905,598 | 9/1959 | Zinke-Allmange | 203/29 |
| 3,278,397 | 10/1966 | Price | 203/38 |
| 3,309,412 | 3/1967 | Sakuragi et al. | 203/9 |
| 3,340,160 | 9/1967 | Waldby | 203/9 |
| 3,405,189 | 10/1968 | Sakuragi et al. | 203/9 |
| 3,551,507 | 12/1970 | Sakuragi et al. | 203/62 |
| 3,681,202 | 8/1972 | Funkhouser | 203/62 |

*Primary Examiner*—Jack Sofer
*Assistant Examiner*—Frank Sever

[57] ABSTRACT

A method of inhibiting the thermopolymerization of isoprene or butadiene in the process of isolation thereof by extractive distillation from a mixture of hydrocarbons obtained in dehydrogenation of isopentane and butane. The method of inhibiting includes, prior to the introduction of said mixture of hydrocarbons and a polar extractant into an extractive distillation metal apparatus, treating the surface of the apparatus with a 1–25% aqueous solution of passivators, viz. nitrites, sulphites or phosphates of alkali metals at a temperature of 20°–100°C. The mixture of hydrocarbons and the polar extractant with an inhibitor of isoprene or butadiene thermopolymerization introduced into the polar extractant are then fed into said apparatus in an amount of 0.01–1% of the extractant weight. The present method makes it possible to reduce markedly the formation of isoprene and butadiene and, hence, to prevent the plugging of the extractive distillation apparatuses with the aforementioned thermopolymers.

5 Claims, No Drawings

METHOD OF INHIBITING THE THERMOPOLYMERIZATION OF ISOPRENE AND BUTADIENE

This is a continuation of application Ser. No. 164,127, filed July 19, 1971.

The present invention relates to methods of inhibiting the thermopolymerization of isoprene and butadiene in a process of their isolation from a mixture of hydrocarbons, produced in dehydrogenation of isopentane and butane, by an extractive distillation technique.

A method is known of inhibiting the thermopolymerization of isoprene and butadiene in the process of their isolation by an extractive distillation technique comprising introducing into the polar extractant a thermopolymerization inhibitor (sulphur, $\beta$-naphtolamine, methylene blue, sodium nitrite) in conjunction with a second component viz. furfural. The inhibitor is introduced in an amount of 0.01–1% of the extractant weight (see U.S. Pat. No. 3309412).

Furfurol is intended to stabilize the polar extractants, e.g. dimethyl formamide and dimethyl acetamide which are susceptible to hydrolysis with formation of acids.

A disadvantage of the known method is that a marked amount of isoprene or butadiene thermopolymers is yielded in metal apparatuses for the extractive distillation, especially at elevated temperatures (120°–150°C) which results in plugging said apparatuses with the aforementioned thermopolymers.

Thus, in thermopolymerization of a 20% solution of isoprene in dimethyl formamide placed in ampoule with iron shavings into which there is also introduced a thermopolymerization inhibitor, viz. sodium nitrite in an amount of 0.02% and furfural in an amount of 1% of the entire mixture weight, the yield of the thermopolymer at 150C during 20 hours of reaction amounted to 12% based on the monomer.

It is an object of the present invention to provide a method of inhibiting the thermopolymerization of isoprene or butadiene in the process of isolating them from a mixture of hydrocarbons, produced by dehydrogenation of isopentane or butane, by extractive distillation, which makes it possible to reduce markedly the isoprene and butadiene thermopolymer formation and hence, to prevent the plugging of the extractive distillation apparatuses with the afore-mentioned thermopolymers.

In accordance with these and other objects, the invention includes prior to introducing a mixture of hydrocarbons and a polar extractant into the extractive distillation metal apparatus, treating the apparatus surface with a 1–25% aqueous solution of a passivator, viz. nitrites, sulphites and phosphates of alkali metals, at a temperature of 20°–100°C, whereafter into the apparatus there are fed a mixture of hydrocarbons and a polar extractant with an isoprene or butadiene thermopolymerization inhibitor introduced into said polar extractant in an amount of 0.01–1% of the extractant weight.

A protective layer is formed on the apparatus surface treated with the passivators, said layer eliminating the catalytic action of the surface, which action leads to the undesirable thermopolymerization of isoprene or butadiene when these monomers are isolated from the hydrocarbon mixture.

The effect attained by the preliminary passivation of the apparatus surface can be enhanced by a direct introduction of passivators into the polar extractant in an amount of 0.02–0.1% of the extractant weight during the process of isolating isoprene or butadiene from the mixture of hydrocarbons.

In this way, the effect produced on the metal surface by treating it with an aqueous solution of a passivator is stabilized.

In addition, the introduction of regulators of the molecular weight of isoprene or butadiene thermopolymers in the process of their isolation from a mixture of hydrocarbons contributes to the accomplishment of the object of the present invention, aliphatic monohydric alcohols, aliphatic monohydric nitrated alcohols, aliphatic amino alcohols and orthonitrophenol in an amount of 0.02–0.2% of the extractant weight being used as the molecular weight regulators.

The use of molecular weight regulators reduces the molecular weight of isoprene or butadiene thermopolymers and enhances their solubility in the extractant which is conducive to eliminating the plugging of the extractive distillation apparatuses.

To prevent acid formation when use is made of readily hydrolyzable substances such as technical dimethyl formamide as the polar extractant, it is advisable, in the process of isolating isoprene or butadiene from a mixture of hydrocarbons, to introduce aliphatic or cylic ketones into the polar extractant in an amount of 0.02–0.2% of the extractant weight.

As the materials entering the extractive distillation system often contain some quantity of water which hydrolyzes the extractive agent, only the aforementioned measures eliminate the influence of acids which enhance the plugging of the extractive distillation apparatuses with isoprene or butadiene thermopolymers.

Also, the aforementioned aliphatic or cyclic ketones can serve as molecular weight regulators as well if they are introduced into the polar extractant in an amount of 0.2–1% of the extractant weight during the isolation of isoprene or butadiene from a mixture of hydrocarbons by extractive distillation.

In the process of isolating isoprene or butadiene from a mixture of hydrocarbons, it is preferably to introduce sodium fluoride, sodium thiocyanate or $\alpha$, $\alpha$-dipyridyl into the polar extractant in an amount of 0.01–0.2% of the extractant weight.

Possessing high complex-forming activity with respect to the ions of variable metals, these substances neutralize the catalysing of the thermopolymerization action in case these ions are introduced with the technical extractant or penetrate into the extractant from the surface of the extractive distillation metal apparatus.

As indicated above, prior to the feed of the hydrocarbons, the metal surface of the extractive distillation apparatus is treated with an aqueous solution of passivators, viz. nitrites, sulphites and phosphates of alkali metals, aqueous solution of diverse concentration (from 1 to 25%) being employed and the treatment of the surface being conducted at a temperature of 20°–100°C for 2–50 hours.

For example, sodium nitrite, sulphur, diphenylamine, parahydroxydiphenylamine, $\beta$-naphtholamine may be used as the inhibitor of isoprene and butadiene thermopolymerization in the present method. The inhibitor concentration is selected in the range of from 0.01 to 1.0% of the extractant weight. Out of the aforementioned substances proposed as molecular weight regulators, use is made of orthonitrophenol, aliphatic monohydric alcohols, e.g. butanol, hexanol, heptanol, octanol, n-amyl alochol; aliphatic monohydric nitrated alcohols, e.g. nitroethanol, nitrobutanol, nitropentanol, nitropropanol; aliphatic amino alcohols, e.g. monoethanolamine, diethanolamine, triethanolamine, butanolamine, propanolamine.

As the aforementioned ketones, in the present method, use is made, for example, of acetone, methyl ethyl ketone, methyl isopropyl ketone, diethyl ketone, and as the cyclic ketones use is made of cyclopentanone, cyclohexanone, cyclooctanone, etc.

As mentioned above, the isolating of isoprene or butadiene from the mixture of hydrocarbons is effected in the presence of polar extractants and as said extractants, use is made of such high-boiling solvents as, for example, dimethyl formamide, dimethyl acetamide and N-methylpyrrolidone.

For a better understanding of the present invention hereinbelow are given by way of illustration the following examples of inhibiting the thermopolymerization of isoprene or butadiene in laboratory conditions simulating the conditions of inhibiting the thermopolymerization of isoprene or butadiene in the commercial process of their isolation by a method of extractive distillation.

EXAMPLE 1

A 20% solution of isoprene in dimethyl acetamide was charged in ampoules, which were preliminarily charged with iron shavings taken in a quantity sufficient for their specific surface amounting to 2 cm$^2$/cm$^3$. Prior to being placed into the operational ampoules the shavings were treated with a 5% aqueous solution of sodium nitrite at a temperature of 90°C for 4 hours. In control tests, a 20% solution of isoprene in dimethyl acetamide was charged onto untreated shavings. Into all ampoules (operational and control) there was introduced an inhibitor viz. parahydroxydiphenyl amide in an amount of 0.1% of the solvent weight.

The mixture in the ampoules was thermostated at a temperature of 150°C for 20 hours, whereupon the monomer and solvent were distilled off in vacuo.

The average yield of the polymer (dry residue) with treated shavings was 2.2% and with untreated shavings was 15% of the monomer weight.

EXAMPLE 2

A 20% solution of isoprene in dimethyl formamide was charged into ampoules containing shavings passivated as described in Example 1.

The polar solvent used contained 2.5% of water.

In operational tests, 0.17 wt. % of cyclohexanone was introduced into the solvent; the control ampoules did not contain ketone. As the inhibitor, sodium nitrite in an amount of 0.01% of the solvent weight was introduced into all ampoules.

The tests and analysis were carried out as described in Example 1. The yield of the polymer in the presence of cyclohexanone was 2.0% and without the ketone addition 3.5% of the monomer weight.

EXAMPLE 3

A 25% solution of butadiene in N-methylpyrrolidone was placed over shavings treated with a 1% aqueous solution of sodium nitrite at a temperature of 100°C for 40 hours.

Into all ampoules an inhibitor viz. N-naphtholamine was introduced into the solvent in an amount of 0.1% of the solvent weight.

Unlike the control ampoules, into the operational ampoules there was introduced nitroethanol in an amount of 1% of the solvent weight.

The tests and analysis were performed in conditions of Example 1 with the only difference that before the ampoules were evacuated, their content was passed through filters built in the ampoules. This procedure made it possible to separate the insoluble part of the polymer from the soluble portion.

The average yield of the polymer (dry residue) in operational ampoules was 0.3% and in control ampoules 1.5% of the monomer weight.

EXAMPLE 4

A 20% solution of butadiene in dimethyl acetamide was placed over iron shavings preliminarily treated with a 10% aqueous solution of sodium phosphate at a temperature of 40°C for 10 hours. Into the operational and control ampoules there were introduced the thermopolymerization inhibitor, viz. parahydroxydiphenylamine in an amount of 0.2% and acetone in an amount of 0.1% of the solvent weight. Into the operational ampoules there was also introduced sodium rhodanide in an amount of 0.05% of the solvent weight.

The tests and analysis were carried out in conditions indicated in Example 1, but the temperature of thermostating the mixture was 140°C.

The yield of the polymer in operational tests was 2%, in control tests 3% of the monomer weight.

EXAMPLE 5

A 25% solution of butadiene in dimethyl acetamide was placed over iron shavings treated with a 20% aqueous solution of sodium phosphate at a temperature of 80°C for 12 hours.

Into all ampoules there was introduced a thermopolymerization inhibitor, viz. sulphur in an amount of 0.15% and cyclohexanone in an amount of 1% of the solvent weight. Into the operational ampoules there was introduced, in addition, $\alpha$, $\alpha$-dipyridyl in an amount of 0.15% of the solvent weight.

The tests and analysis were carried out in conditions indicated in Example 1, but the temperature of thermostating the mixture was 160°C.

The average yield of the polymer (dry residue) in the ampoules containing $\alpha,\alpha$-dipyridyl was 0.7% and in the ampoules free of said addition 2.1% of the monomer weight.

EXAMPLE 6

A 20% solution of isoprene in technical N-methylpyrrolidone was placed in ampoules over iron shavings preliminarily passivated with a 10% aqueous solution of potassium sulphite at a temperature of 80°C for 8 hours.

Into all ampoules there was introduced an inhibitor, viz. diphenylamine in an amount of 0.4%, cyclopentanone in an amount of 0.08% and orthonitrophenol in an amount of 0.08% of the solvent weight.

The mixtures in the ampoules were thermostated at a temperature of 155°C for 20 hours.

In a part of the ampoules, prior to evacuating thereof and distilling the monomer and solvent, the mixture was filtered through filters built in the ampoules. The yield of the polymer (dry residue) in the ampoules where the mixture was preliminarily filtered amounted to 0.5% and in the ampoules where the mixture was not filtered amounted to 4% of the starting monomer

EXAMPLE 7

A 20% solution of isoprene in technical dimethyl formamide was placed in ampoules preliminarily filled with passivated metal shavings. The passivation was effected with a 25% aqueous solution of sodium phosphate at a temperature of 60°C for 2 hours.

Into the operational ampoules there was introduced an inhibitor, viz. sodium nitrite in an amount of 0.02%, monoethanolamine in an amount of 0.08%, sodium fluoride in an amount of 0.1% and methyl ethyl ketone in an amount of 0.2% of the solvent weight.

In to the control ampoules, a 20% solution of isoprene in technical dimethyl formamide was placed over untreated metal shavings. An inhibitor, viz. sodium nitrite was added to the mixture in an amount of 0.02% of the solvent weight.

In all ampoules, the mixture was thermostated at a temperature of 145°C for 20 hours.

The average yield of the polymer on vacuum distillation of the monomer and solvent amounted to in operational tests 0.05% and in control tests 12% of the monomer weight.

EXAMPLE 8

In conditions of Example 7, n-hexyl alcohol in an amount of 0.2% of the solvent weight was employed instead of monoethanolamine in the operational tests. The polymer yield in the operational ampoules was 0.07% of the monomer weight.

We claim:

1. In a process for inhibiting the thermopolymerization of a feed during the extractive distillation of said feed, said feed comprising members selected from the group consisting of isoprene and butadiene produced in a dehydrogenation reaction, the improvement comprising, contacting the internal metallic surfaces of the apparatus used for said extractive distillation, with a solution, prior to the introduction of said feed into said apparatus, said solution comprising a 1–25 WT% aqueous solution of passivators selected from the group consisting of sodium nitrite, potassium nitrite, sodium sulfite, potassium sulfite, sodium phosphate and potassium phosphate, said solution having a temperature of about 20°–100°C, said improvement further comprising, introducing said feed and a polar extractant into said apparatus after said contacting, said extractant selected from the group consisting of dimethyl acetamide, dimethyl formamide and n-methylpyrrolidone, said extractant containing 0.01–1.0 wt% of an inhibitor selected from the group consisting of sodium nitrite, n-naptholamine, parahydroxydiphenylamine, sulphur and diphenylamine.

2. The method of claim 1, wherein said passivators are present in said polar extractant in an amount of from 0.02–1.0% of the extractant weight.

3. A method according to claim 1, wherein members of the group consisting of methyl ethyl ketone, cyclopentanone, cyclohexanone and acetone are additionally present in said polar extractant in an amount of from 0.02–0.2% of the extractant weight.

4. The method according to claim 1, members of the group consisting of methyl ethyl ketone, cyclopentanone, cyclohexanone and acetone are additionally present in said polar extractant in an amount of from 0.2–1.0% of the extractant weight, said member serving as a molecular weight regulator for isoprene and butadiene.

5. The method according to claim 1, wherein members selected from the group consisting of sodium fluoride, sodium thiocyanate and $\alpha, \alpha$-dipyridyl are additionally present in said polar extractant in an amount of from 0.01–0.2% of the extractant weight.

* * * * *